United States Patent [19]

Zuest et al.

[11] Patent Number: 4,715,817

[45] Date of Patent: Dec. 29, 1987

[54] DENTURE ATTACHMENT STRUCTURE AND METHOD

[76] Inventors: Max Zuest, 595 San Fernando, San Diego, Calif. 92106; Paul Zuest, 13531 Orange Blossom La., Poway, Calif. 92064

[21] Appl. No.: 876,265

[22] Filed: Jun. 19, 1986

Related U.S. Application Data

[63] Continuation-in-part of Ser. No. 765,811, Aug. 15, 1985, abandoned.

[51] Int. Cl.$^4$ ............................................. A61C 13/22
[52] U.S. Cl. ..................................... 433/181; 433/177
[58] Field of Search ............... 433/181, 182, 183, 169, 433/170, 180

[56] References Cited

U.S. PATENT DOCUMENTS

| | | | |
|---|---|---|---|
| 1,522,233 | 1/1925 | Feinberg. | |
| 2,347,340 | 4/1944 | Smallen | 32/5 |
| 2,803,060 | 8/1957 | Weiss | 32/5 |
| 3,535,787 | 10/1970 | Korte | 433/182 |
| 4,362,509 | 12/1982 | Sulc | 433/181 |
| 4,579,528 | 4/1986 | Staubli | 433/181 |

FOREIGN PATENT DOCUMENTS

| | | |
|---|---|---|
| 1566198 | 7/1970 | Fed. Rep. of Germany. |
| 8428139 | 12/1984 | Fed. Rep. of Germany. |
| 546065 | 2/1974 | Switzerland. |

OTHER PUBLICATIONS

"Stern G/C Attachment" Stern Dental Co. Inc. Mt. Vernon N.Y., 6/1979.

Primary Examiner—Robert Peshock
Attorney, Agent, or Firm—Brown, Martin, Haller & Meador

[57] ABSTRACT

An attachment structure for securing a denture in an oral cavity comprises an insert member for securing to the denture and a retainer member for mounting in a cut-out in an existing tooth. One of the members has an elongate channel and the other member has a corresponding elongate tongue for sliding engagement in the channel in the direction of insertion of the denture in the oral cavity. The channel and tongue have cooperating interengageable snap-fit formations at their lower end which are elongated in a direction transverse to the tongue and channel.

19 Claims, 10 Drawing Figures

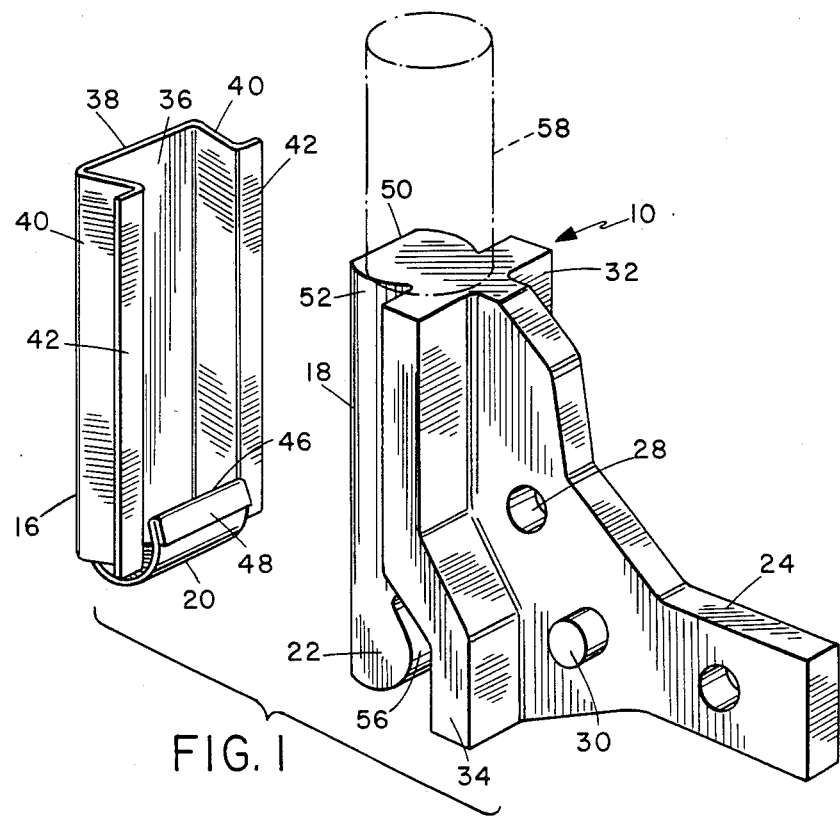
FIG. 1
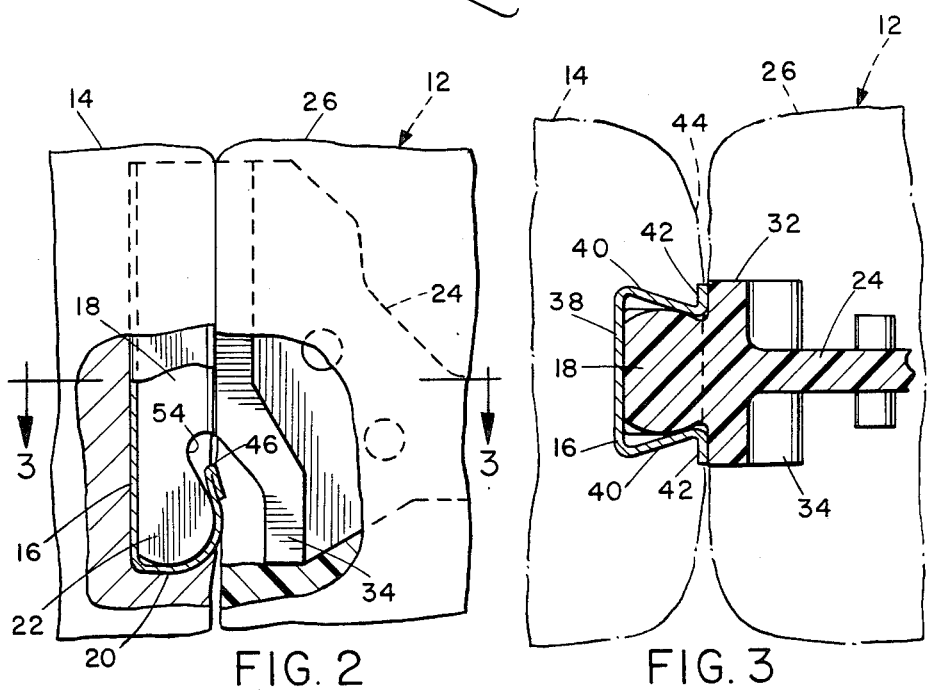
FIG. 2
FIG. 3

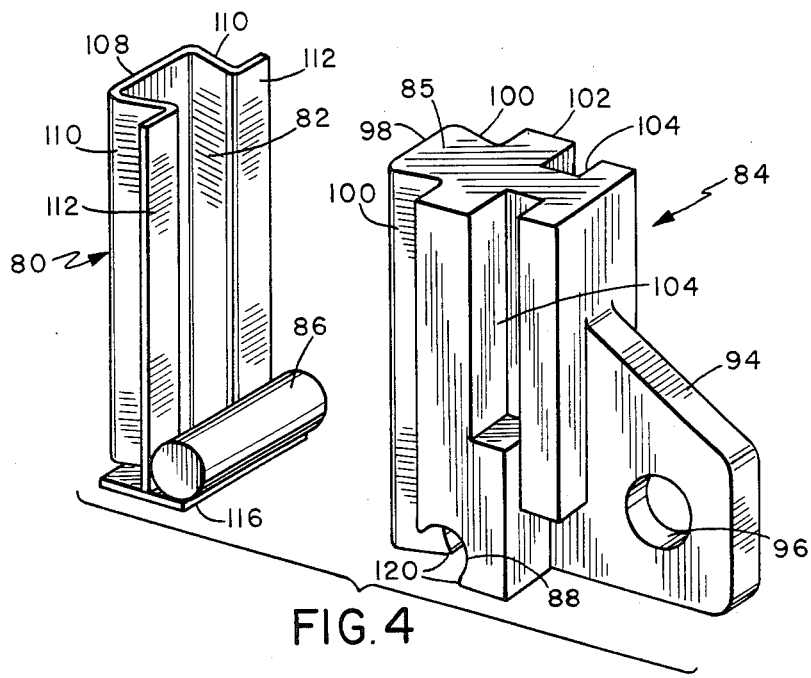
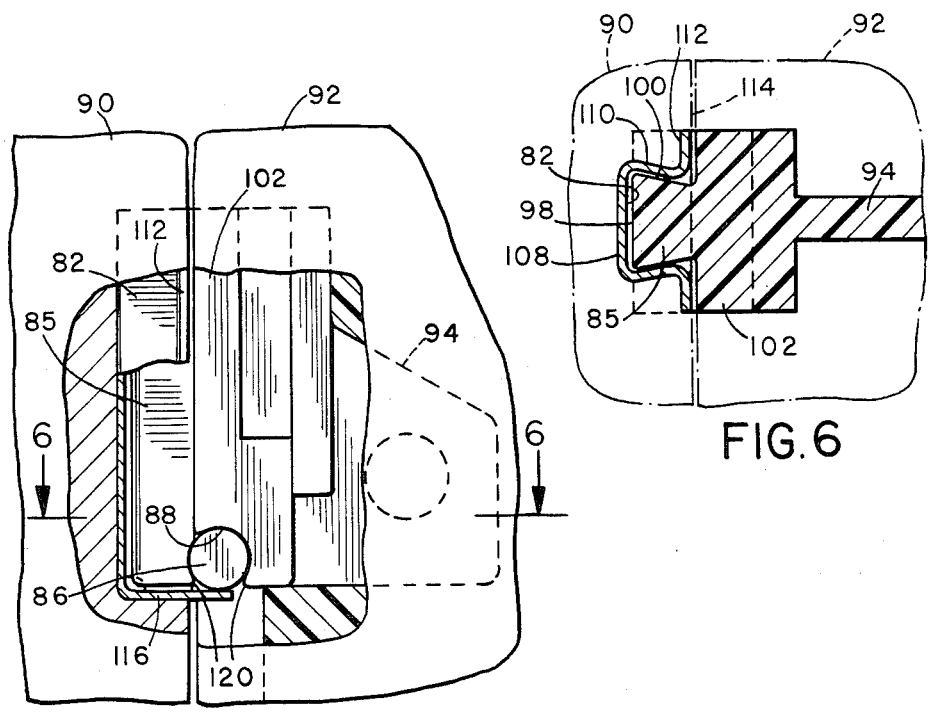

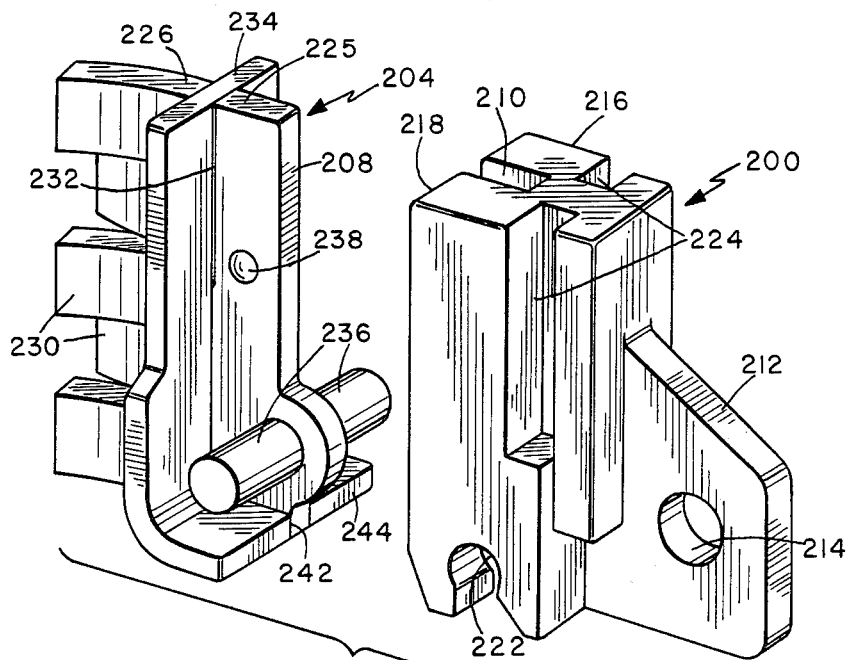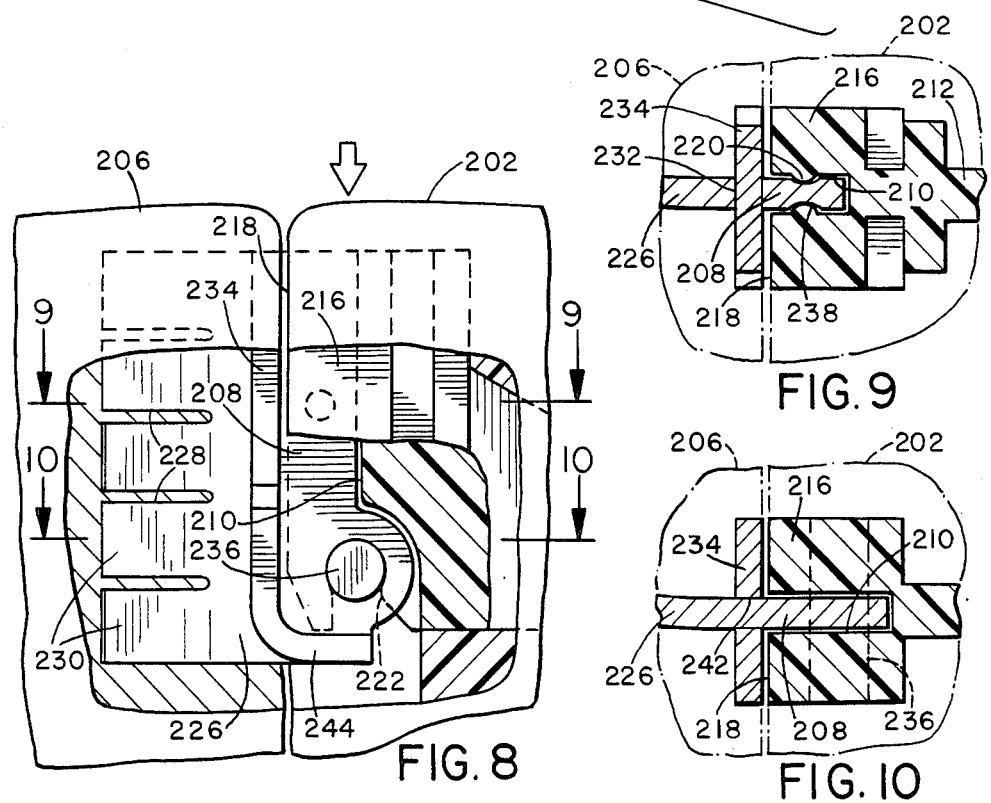

DENTURE ATTACHMENT STRUCTURE AND METHOD

This is a continuation-in-part of application Ser. No. 765,811 filed Aug. 15, 1985 and now abandoned.

BACKGROUND OF THE INVENTION

The present invention relates to a denture attachment structure or anchor for anchoring a denture in an oral cavity, and to a method for securing the structure to an existing tooth or teeth.

In our U.S. Pat. No. 4,547,159 to the same Applicants which is entitled "Snap-In Anchor for Denture," filed on Dec. 19, 1984, an anchor is described which comprises a pin member secured to a denture and a channel member retained in an existing tooth. The pin member has a ball at one end which is a snap-fit in a correspondingly shaped socket at the end of the channel member. The pin member is a frictional sliding fit in the channel member and is retained in place by the resilient side walls of the channel member. The arrangement allows limited side to side movement of the denture to accommodate jaw motions so as to reduce the stress on the tooth or teeth to which the denture is anchored.

In other denture attachment structures the securing means usually involves a groove or channel formed in a ceramic or metal crown cemented on the existing teeth and a matching tongue or pin built into the denture, which slides into the channel as the denture is fitted. An attachment of this type is show, for example, in U.S. Pat. No. 4,362,509 of Sulc. This type of attachment is fairly expensive and often involves resilient inserts to allow very limited movement of the denture. The inserts are subject to wear.

BACKGROUND OF THE INVENTION

According to one aspect of the present invention an attachment structure or anchor assembly is provided for securing a denture in an oral cavity, which comprises a retainer member for securing directly in a cut-out in an existing tooth, and an insert member for securing to a denture. One of the members has an elongate channel and the other member has a corresponding elongate tongue for sliding engagement in the channel in the direction of insertion of the denture in the oral cavity. The tongue and channel have cooperating snap-fit formations at their lower ends which are preferably of at least partially cylindrical shape and which extend in a direction transverse to the axis of the tongue and channel. The denture is anchored to the existing tooth by sliding the tongue into the channel and snapping the cooperating snap-fit formations together.

Preferably, the channel or sleeve has resilient side walls which grip the pin member for stability but allow very limited movement of the denture to accommodate jaw motions. According to the present invention the snap-fit formations are elongated in a direction traverse to the longitudinal axis of the channel and tongue, i.e. transverse to the path of insertion of the pin member in the channel member. This provides a greater retention force than a ball and socket type of attachment, so that the overall dimensions of the attachment structure can be reduced. Thus this type of attachment structure is particularly suitable for attachment to relatively small teeth such as biscuspids, since the channel and tongue can be shorter while the positive snap engagement between the transversely elongated formations provides sufficient retentive force to retain the denture in place during normal jaw motions.

Preferably, the formations comprise a socket and head of corresponding barrel-like shape. The channel and tongue may be of any suitable cross sections for providing a frictional sliding fit between the members, but the channel preferably has a flat back wall so that it is less invasive of the tooth in which it is retained. The tongue will then have a corresponding flat front face for engaging the back wall of the channel when it slides into place. The channel preferably has in-turned side walls for resiliently gripping the tongue and also for helping to retain the channel in the tooth.

According to another aspect of the present invention a method is provided for mounting a denture in an oral cavity. An insert member is secured to one end of the denture. The insert member is releasably secured to corresponding retainer member by sliding the tongue on one of the members into the channel on the other member until the cooperating formations at the lower ends of the tongue and channel snap into engagement. A vertically extending cut-out is formed in the side face of a tooth facing the site at which the denture is to be mounted, the cut-out being shaped to correspond to the shape of the retainer member. Bonding material is then placed in the tooth cut-out and preferably also on at least the lower end of the retainer member. The retainer member carrying the attached denture via the insert member is then inserted into the cut-out so that the denture is properly aligned in the oral cavity.

The channel and tongue may be provided on the retainer and insert member, respectively, or vice versa. The interengageable formations preferably comprise corresponding generally cylindrical or barrel-like head and socket formations at the lower end of the channel and tongue. In one arrangement, the socket is provided at the lower end of the channel and the head is at the lower end of the tongue. In an alternative arrangement, the head comprises a cylindrical projection at the lower end of the channel and the tongue is provided with a corresponding part-cylindrical cut-out of its lower end which snaps over the head when the tongue is fully inserted in the co-operating channel.

Thus, according to the present invention a denture attachment structure and method is provided which allows a positive snap lock between the denture and adjacent teeth while allowing limited movement of the denture with jaw motions, and which allows the dimensions of the necessary cut-out in an existing tooth to which the denture is to be anchored to be reduced, thus allowing it to be anchored securely to relatively small teeth such as biscuspids.

BRIEF DESCRIPTION OF THE DRAWINGS

The above and other aspects of the present invention will be more clear from the following detailed description of some preferred embodiments of the present invention, taken in conjunction with the accompanying drawings, in which like reference numerals refer to like parts and in which:

FIG. 1 is a perspective view of an attachment structure according to a first embodiment of the present invention:

FIG. 2 is a side elevation view, with portions cut away, showing the structure installed to anchor a denture to an existing tooth;

FIG. 3 is a sectional view on the line 3—3 of FIG. 2;

FIG. 4 is a perspective view of an attachment structure according to a second embodiment of the present invention;

FIG. 5 is a side elevation view of the structure of FIG. 4, partially cut away, showing the structure installed to anchor a denture to an existing tooth;

FIG. 6 is a sectional view taken on the line 6—6 of FIG. 5;

FIG. 7 is a perspective view showing an attachment structure according to a third embodiment of the invention;

FIG. 8 is a side elevation view, with portions cut away, showing the attachment structure of FIG. 7 anchoring a denture to an existing tooth;

FIG. 9 is a sectional view on the line 9—9 of FIG. 8; and

FIG. 10 is a sectional view taken on the line 10—10 of FIG. 8.

DESCRIPTION OF THE PREFERRED EMBODIMENT

FIGS. 1 to 3 show a first embodiment of a denture attachment structure or anchor 10 according to one aspect of the present invention for anchoring one end of a denture 12 to an existing tooth 14. The denture may be full or partial, and include teeth on one or both sides of the arch. One or more of the attachment structures shown in FIGS. 1 to 3 may be used to anchor one or more respective end teeth of the denture to adjacent existing teeth in the manner described below.

As best shown in FIG. 1, the attachment structure is in two parts, comprising retainer member 16 and an insert member 18. The retainer member 16 has an open-sided elongated channel 36 and the insert member has a corresponding tongue or pin 52 for frictional sliding engagement in the channel 36.

Cooperating snap-fit formations are provided at the lower end of the tongue and socket as seen in FIGS. 1 and 2. The formations comprise an upwardly facing socket 20 provided at the lower end of channel 36, and a head 22 at the lower end of pin or tongue 52 which is designed to be a snap fit in the socket 20.

The head and socket are elongated transverse to the longitudinal axes of the tongue and channel and are preferably of barrel-like or part cylindrical shape as shown in the drawings. When the tongue is fully engaged in the channel as shown in FIG. 2, limited rocking movement is provided between the two members about the longitudinal pivot axis of the head and socket, as will be explained in more detail below.

The insert member 18 has a radially projecting retaining tail portion 24 which is embedded in an end artifical tooth 26 of a denture so that the insert member projects to one side of the end face of the tooth. Suitable holes 28 and studs 30 are provided on the tail portion to provide maximum contact and interengagement with the material of the denture as it sets. Any suitable number and arrangement of studs and holes may be provided in the tail portion 24.

A transverse end wall 32 is provided between the tail portion and tongue 52 of the insert member which is arranged to lie flush with the end face of tooth 26 when the tail portion is embedded in the tooth, as shown in FIGS. 2 and 3. The end wall extends along a portion of the tongue with an offset portion 34 at its lower end spaced radially from the tongue 34 to clear the head 22.

The retainer member channel 36 receives and retains the tongue between flat back wall 38 and in-turned or indented side walls 40. Outwardly turned flanges 42 at the outer edges of side walls 40 are arranged to lie substantially flush against the end wall 44 of an existing tooth in which the channel member is secured, as best shown in FIG. 3. The socket 20 is preferably formed by a turned up extension of back wall 38. The extension is curved upwardly and indented at its upper end 46 for a snap engagement to retain the head 22 against accidental separation. The extension may be suitably bonded or welded at each side to adjacent portions of the side flanges 42. The weld preferably extends at least 2/3 of the way between the lower and upper ends of the socket. The upper end 46 may have a folded back lip 48 as shown to add strength to the upper edge of the socket for retaining the head in the socket.

The retainer member is preferably made from thin relatively resilient material such as stainless steel, and the insert member is preferably of a suitable plastics material such as nylon.

The insert member 18 may have a tongue of any suitable cross-sectional shape for frictional sliding engagement in the channel member. In the preferred embodiment shown in FIGS. 1 to 3 it has a flat front face 50 for engagement with the flat back wall of the channel, and rounded or part cylindrical side faces for retention behind the in-turned side walls 40 of the channel member, as shown in FIG. 3. The tongue, end wall and tail portion may be formed as a one piece integral moulding. The head 22 comprises a part cylindrical formation at the lower end of the tongue formed by an indent 54 and outwardly rounded portion 56 facing offset portion 34 of the end wall. The tongue may have an upwardly extending projection 58 of cylindrical shape, cross section, as shown in dotted outline in FIG. 1, to aid in holding the denture during initial insertion and alignment in an oral cavity. Alternatively, the end wall may have opposed grooves, as described in more detail below with reference to the other embodiments of the invention, for engagement by an alignment fork (not shown) to hold the insert member during insertion of the denture.

The fully seated connection between the retainer and insert member is shown in FIGS. 2 and 3. The retainer member is secured in a suitably prepared cut-out in an existing tooth adjacent the denture site, with the in-turned side walls 40 having a wedge-like engagement with the surrounding tooth or filling material to aid in retaining the member in the tooth. The offset portion 34 of end wall 32 is designed to allow sufficient clearance for the socket 20 when the head 22 is shaped into it as shown in FIG. 2.

When the tongue is fully seated in the channel as shown in FIGS. 2 and 3, the side walls 40 of the channel resiliently grip the tongue in place, with the socket and head having a pivotal engagement allowing a very limited amount of relative lateral movement of the denture to accommodate jaw motions during chewing, the snap fit between the socket and head preventing accidental separation of the members but at the same time allowing the denture to be removed and replaced for cleaning or repair. Because of the transverse barrel-like shape of the pin and socket, providing and elongated line of retention transverse to the path of insertion of the insert member and denture, and thus also transverse to the line of connection between the denture and existing tooth, the channel and tongue can be shorter in the longitudinal or vertical direction while still providing sufficient retention force to avoid or reduce the risk of accidental separation. Thus, the overall dimensions of the attachment structure can be reduced, making it easier to insert in smaller teeth such as bicuspids. The attachment structure may in fact be one third or more smaller in all dimensions than an attachment structure of the type involving a spherical ball and socket connection. The flat back face of the channel and the reduced overall dimensions make it less invasive of the existing tooth in which it is mounted and thus less likely to cause inflammation or other problems.

If necessary, an additional retaining sleeve may be provided for retaining the member 16 in the tooth more securely. This would be shaped to slide over the back wall and indented side walls of the channel member and have a rearwardly projecting flat lug or tab adjacent its top end which would project into a corresponding cut-out could in the top face of the tooth. The cut-out then be filled with suitable filling material to secure the lug, with the indented side walls of the retaining sleeve providing additional security against the retainer member pulling out of the tooth. The retaining sleeve is preferably shorter than the channel and slides over it until the lug engages in the tooth cut-out. Once the parts are correctly positioned, the channel can be cut to the appropriate length. The lug may also be shortened if necessary according to the dimensions of the tooth. The lug may have openings or studs for maximum engagement with the surrounding filling material.

FIGS. 4 to 6 of the drawings illustrate an alternative embodiment of the attachment structure according to the present invention. The structure comprises a retainer member 80 having an elongate channel 82 and an insert member 84 having an elongate tongue 85 which is a frictional sliding fit in the channel 82. The structure is similar to that of FIGS. 1 to 3, except that the cooperating snap-fit formations at the lower ends of the tongue and channel are reversed. Thus, the channel 82 has a transverse barrel-like or cylindrical-shaped head 86 at its lower end while the tongue 85 has a corresponding downwardly directed part-cylindrical transverse cut-out or socket 88 at its lower end. When the tongue is fully inserted in the channel as indicated in FIG. 5 the socket will snap fit over the head 86.

Retainer member 80 is designed to be mounted in a suitably shaped cut-out in an existing tooth 90 alongside a site where a denture is to be mounted, while insert member 84 is designed to be embedded in an end tooth 92 of a denture so that the tongue 85 projects to one side of the end face of that tooth.

As shown in FIGS. 4 and 5, the insert member, which is preferably a one-piece integral molding of plastics material such as nylon, has a projecting tail portion 94 for embedding in the denture material. The tail portion has one or more openings or studs 96 to provide maximum contact to anchor the insert member to the denture, as in the previous embodiment. The tongue 85 has a forward flat wall 98, indented side walls 100, and a transverse flange portion 102 which projects outwardly at each side of the tongue. The front face of flange portion 102 is designed to lie flush with the end face of denture 92 when the insert member is embedded in the denture material, as best seen in FIG. 5. The flange portion 102 is provided on its opposite side faces with oppositely directed indents or grooves 104 which extend along part of the length of the tongue, the purpose of which is described in more detail below. The socket 88 in the tongue comprises a transverse, part-cylindrical downwardly facing cut-out 106 at the lower end of flange portion 102.

The retainer member 80 is preferably made from a relatively thin, plate-like material such as stainless steel plate. The member has a flat back wall 108 and in-turned side walls 110 defining the rear and side walls of the channel 82 which is of corresponding cross-section to tongue 85 for receiving the projecting portion of tongue 85. Outwardly turned lips or flanges 112 at each side of the channel are designed to lie substantially flush with the end wall 114 of a tooth 90 in which the member 80 is secured, as shown in FIG. 5.

The lower end wall 116 of the channel projects outwardly from the front open face of the channel, and a barrel or bar-like head 86 of generally cylindrical cross-section is suitably bonded to the projecting end of lower wall 116. The diameter of head 86 is substantially equal to the diameter of socket 88, so that when projecting tongue 85 is fully inserted in the channel, the socket 88 will snap over the head 86 to secure the two members together. The head 86 may, for example, comprise a length of wire welded or otherwise bonded to the projecting end of lower wall 116 and the flanges 112. In one specific example the head 86 was of 0.042 inch diameter stainless steel wire, and the socket 88 was also of substantially 0.042 inches diameter.

As can be seen in FIG. 5, the socket 88 has a downwardly facing opening through which the head 86 will be inserted which has a width less than the diameter of socket 88. In-turned lips 120 on each side of opening 118 will be resiliently compressed as the head is forced through the opening and will snap back when the head is fully engaged in the socket to retain it in place.

The fully seated connection between the retainer and insert members is shown in FIGS. 5 and 6. The retainer member is secured in a suitably prepared cut-out in an existing tooth, with the in-turned side walls having a wedge-like engagement with the surrounding tooth or filling material to aid in retaining the member in the tooth. As in the previous embodiment, the channel and projecting portion of the tongue are of substantially corresponding generally wedge-like cross section so that when the tongue is inserted in the channel, the inturned side walls will resiliently grip the tongue in place. The head and socket will have a pivotal engagement to allow a very limited amount of lateral movement of the denture to accommodate jaw motions during chewing. The snap fit and tongue and channel engagement will act to prevent accidental separation of the members but at the same time will allow the denture to be removed and replaced for cleaning and repair. As in the first embodiment, the transverse barrel-like shape of the head and socket provides an elongated line of retention in a direction transverse to the tongue and channel connection between the denture and tooth, so that the tongue and channel can be of smaller dimensions while the attachment will still provide sufficient retention force to avoid or substantially reduce the risk of accidental separation. Thus the attachment structure is suitable for use with relatively small teeth.

As in the first embodiment, the retainer member may be used with an additional retaining sleeve or stabilizer comprising a generally flat plate-like member having a cut-out at one end shaped to slide over the outer walls of the channel, and a rearwardly projecting flat lug or tab for projecting into a corresponding cut-out in the upper face of a tooth or filling once the correct height for the sleeve on the channel has been determined. The retainer member can then be cut to the appropriate length.

FIGS. 7 to 10 of the drawings show a further modified embodiment of the attachment structure according to this invention. The attachment structure of FIGS. 7 to 10 can be of equivalent or smaller dimensions than those shown in FIGS. 1 to 6 and can thus be sized for use with even smaller teeth.

The attachment structure of FIGS. 7 to 9 is again in two basic parts, comprising an insert member 200 for securing to an end tooth 202 of a denture, and a retainer member 204 for securing in an appropriate cut-out in an existing tooth 206, which may be real or artificial, adjacent the site where the denture is to be mounted. In this embodiment the tongue and channel are reversed, with a projecting tongue 208 on retainer member 204 being a frictional sliding fit in a corresponding slit-like channel 210 on insert member 200 in the direction of insertion of the denture in the oral cavity.

As best seen in FIGS. 7 and 8, insert member 200 is preferably a one-piece integral molding, suitably of plastics material such as nylon, having a tail portion 212 for embedding in the denture material for improved stability. The tail portion 212 has one or more holes or studs 214 for improved contact and rigidity of the connection, as in the previous embodiments. The insert member has a widened head portion 216 with a substantially flat front face 218 designed to lie flush with the end face of denture tooth 202 when the insert member is correctly embedded as shown in FIG. 9. Thin elongate slit or channel 210 is located in the central portion of front face 218. Located approximately half way down the channel side walls are opposed bumps or raised protrusions 220 as best seen in FIG. 9.

As in the previous embodiment, a part cylindrical cut-out or socket 222 extending transverse to the longitudinal axis of the channel is located at the lower end of head portion 216 so as to extend outwardly from opposite sides of the channel. Oppositely directed grooves or indents 224 extend on opposite sides of the head portion 216 along part of its length, the purpose of which is described in more detail below.

The retaiber member 204 is of a suitable thin sheet material such as stainless steel sheet, and is preferably formed in two parts as indicated in the drawings. The first part 225 is a generally flat plate like member having a forward end comprising the tongue 208 for sliding engagement in channel 210 as indicated in FIG. 8, and rearward end 226 having slits 228 separating fingers or fins 230 which may be offset slightly in opposite directions to help retain the member 204 in a tooth cut-out. The part 225 has an upwardly facing slot 232 for receiving the second part 234 as described below. Located at the lower end of tongue 208 are pins or bars 236 which project in opposite directions from opposite faces of tongue 208 and which are shaped to be a snap fit in portions of socket 222 on opposite sides of channel 210 when the tongue is fully inserted in the channel as shown in FIG. 8. The pins may suitably comprise short lengths of stainless steel wire as in the previous embodiment which are suitably welded or otherwise bonded to the lower end of tongue 208.

Thus in this embodiment the interengageable snap fit formations on the tongue and channel comprise projecting pins on opposite faces of the tongue and corresponding socket portions in the lower end of the head portion 216 of insert member 200 which project on opposite sides of the lower end of the channel 210. The tongue 208 also has opposed indents 238 corresponding to protrusions or bumps 220 on channel side walls, and the protrusions will seat in indents 238 as shown in FIG. 9 when the tongue is fully inserted in the channel for added stability.

The second part 234 of retainer member 204 comprises a similar flat sheet-like member having a downwardly facing slot 242 for fitting over slot in the first part to secure the two parts together so that the member 240 forms oppositely directed transverse flanges at the rear of tongue 208 which are arranged to lie flush with the end face of tooth 206 when the retainer member is mounted in the previously prepared tooth cut-out. The member 244 is bent inwardly at its lower end as shown to form a lower wall on which head portion 216 of the insert member sits as shown in FIG. 8 when the two members are secured together.

As in the previous embodiments the insert member is first secured to the retainer member, and the retainer member is then bonded in a suitably prepared cut-out in an existing tooth to secure the denture in place. The pins will snap fit into socket 222 on each side of the channel and will be retained against accidental separation while allowing a small amount of freedom of movement during chewing, for example.

In all of the embodiments described the dimensions of the attachment structure can be relatively small so that the members can be used for securing dentures to small teeth. In one specific example the overall length of the retainer member was of the order of 0.25 to 0.27 inches and the width was approximately 0.12 inches. The retainer member in each embodiment can suitably be formed of stainless steel sheet material and in a specific example sheet of 0.02 inches thickness was used. Thus the necessary cut-out in an existing tooth can be relatively small, reducing the risk of subsequent infection or inflamation.

A method of mounting a denture in an oral cavity using any of the attachment structures described above will now be described. The attachment structure is designed to be placed in a Class II amalgam preparation cut into molar or bicuspid teeth. If necessary, the tooth to which the structure is to be secured can be extended mesially or distally with a composite material to accommodate the depth of the attachment structure. The tooth need not be a natural tooth but may be a crown or other structure, for example.

A cut-out is made in the side face of a tooth adjacent the site at which the denture is to be mounted, the cut-out corresponding in shape and dimensions substantially with the shape of the retainer member, which may be the same as shown in any of FIGS. 1 to 10 of the drawings or of other shapes and dimensions. Where the retainer member of FIGS. 1 to 3 or 4 to 6 is used, the cut-out need not have indented side walls to correspond to the indented side walls of the channel, but may be of square or rectangular section with the wedge shaped gaps being filled with a suitable filling or bonding material.

The cut-out should be aligned as closely as possible with the path of insertion of the planned prothesis, and this may be done by eye. The cut-out is made according to standard dental techniques for filling preparations. A small amount of a suitable bonding material, preferably a light and/or chemical cured composite resin, is then placed on the gingival floor and pulpae wall of the tooth preparation. The resin is also packed on the outer faces of the retainer member. Preferably a minimum of bonding material is used in the indent in the embodiments of FIGS. 1 to 6 to allow for the resilient action of the side walls retaining the tongue in the channel.

The tongue is then snapped into the channel making sure that the tongue is flush against the rear wall of the channel. The retainer member is then seated into the tooth cut-out and aligned with the proper path of prosthesis insertion. This may be done by gripping a suitable extension such as extension 58 shown in FIG. 1 on the insert member, either by hand or using a suitable tool. Alternatively, a removeable alignment tool or fork is used to grip the insert member by insertion in suitable opposed grooves 104 or 224 provided on the insert member as indicated in FIGS. 4 and 7.

Once the denture is correctly positioned, the initially placed resin of bonding material is polymerized or curved according to the manufacturer's instructions to stabilize the attachment structure. The resin material is then built-up and cured in layers until filling of the cut-out is complete.

Once the attachment structure and denture are correctly positioned and secured, the top of the metallic retainer member and plastic insert member may be reduced with a suitable grinding tool until they conform into proper occlusion with the composite resin material. Over contouring may be necessary for proper shaping of the occlusal faces. Prior to this step any upward extension or projection on the insert member to aid in initial mounting of the attachment structure will be sheared or cut off or the alignment fork is withdrawn from the grooves which are then filled.

The above description relates to securing a single attachment structure to an existing tooth. It will be understood that it is not limited to attachment structures or anchors as shown in FIGS. 1 to 10, but may be used in attaching any denture to a tooth via a channel member and snap anchor.

More than one attachment structure may be used with a single prosthesis, by suitable alignment of several attachment structures in both the horizontal and vertical planes.

All the attachment structures on a denture may be seated before the curing step is carried out, or each structure may be secured in the respective cut-out by curing as soon as it is seated, with the insert member being removed for alignment with additional attachment structures.

The denture attachment structure and method of this invention allows substantially stress-free attachment of a prosthesis to any dentition or substitute, and allows one or more attachment structures to be mounted in the correct orientation relatively quickly, accurately and easily.

Although some preferred embodiments of the invention have been described above by way of example, it will be understood by those skilled in the field that modifications may be made to the disclosed embodiments without departing from the scope of the invention, which is defined by the appended claims.

We claim:

1. An attachment structure for securing a denture to an existing tooth or tooth substitute, comprising:
    an insert member for securing to a denture;
    a retainer member for securing in a cut-out in an existing tooth or tooth substitute;
    one of the members having an elongate, open faced channel and the other member having a corresponding elongate tongue which is a frictional sliding fit in the channel in the direction of insertion of a denture in an oral cavity;
    the channel and tongue having cooperating interengageable snap fit formation at their lower ends for snap fit engagement when the tongue is fully inserted in the channel, one of the formations comprising a socket and the other formation comprising a head of corresponding shape to the socket; and
    the head and socket being elongated in a direction transverse to the longitudinal axes of the tongue and channel and each being of length greater than the transverse width of the tongue and channel so that they project outwardly on opposite sides of the tongue and channel.

2. The structure as claimed in claim 1, wherein said head and socket are of corresponding part-cylindrical shape, with their longitudinal axes transverse to the longitudinal axes of the tongue and channel.

3. The structure as claimed in claim 1, wherein said channel has a flat back wall opposite its open side and said tongue has a flat front face for sliding engagement with said back wall when said tongue is inserted in said channel.

4. The structure as claimed in claim 3, wherein said channel has inwardly turned side walls for resiliently gripping said tongue.

5. The structure as claimed in claim 3, wherein said tongue is of part-cylindrical shape and said head comprises a transverse formation of at least partially cylindrical shape at the lower end of said tongue.

6. The structure as claimed in claim 1, wherein said socket comprises a downwardly facing socket on said insert member and said head is provided at the lower end of said retainer member.

7. The structure as claimed in claim 6, wherein said socket is provided at the lower end of said tongue, and said head projects from the lower end of said channel.

8. The structure as claimed in claim 7, wherein said head and said socket are of corresponding at least partially cylindrical cross section.

9. The structure as claimed in claim 8, wherein the head projects outwardly from the lower end of the channel, the tongue including a projecting portion for sliding engagement in the channel and the downwardly facing socket being spaced inwardly from the projecting portion for snap fitting over the head when the tongue is fully engaged in the channel.

10. The structure as claimed in claim 6, wherein the channel and tongue are of corresponding wedge-like cross-section.

11. The structure as claimed in claim 6, wherein said tongue is provided on said retainer member and said channel is provided on said insert member.

12. The structure as claimed in claim 11 wherein said insert member has an elongated thin slit in its front face comprising said channel and said retainer member has a corresponding thin plate-like projection comprising said tongue, said head comprising opposed cylindrical pins projecting from opposite faces of said tongue and said socket comprising corresponding, part cylindrical grooves at the lower end of said insert member extending on opposite sides of said channel.

13. The structure as claimed in claim 12, wherein said tongue and channel each have opposed corresponding interengageable bumps and depressions at corresponding positions along their length for engagement when said tongue is fully inserted in said channel.

14. The structure as claimed in claim 1, wherein said retainer member has rearwardly projecting oppositely angled fingers for anchoring said retainer member in said tooth.

15. The structure as claimed in claim 1, wherein the insert member has elongate grooves on its opposite side faces for receiving the prongs of an alignment fork for use in inserting the structure into a prepared cut-out in an existing tooth.

16. An attachment structure for securing a denture to an existing tooth or tooth substitute, comprising:

an insert member for securing to a denture, the insert member having a lower face which faces downwardly relative to the direction of insertion of the denture in an oral cavity;

a retainer member for securing in a cut-out in an existing tooth or tooth substitute;

one of the members having an elongate, open faced channel and the other member having a corresponding, elongate tongue which is a frictional sliding fit in the channel in the direction of insertion of a denture in an oral cavity;

the channel and tongue having cooperating snap-fit formations at their lower ends for snap-fit engagement when the tongue is fully inserted in the channel, one of the formations comprising a socket and the other formation comprising a head of corresponding shape to the socket;

the head and socket being elongated in a direction transverse to the longitudinal axes of the tongue and channel; of length greater than the transverse width of the tongue of channel so that they project outwardly on opposite sides of the tongue and channel the socket comprising a part cylindrical socket on the lower face of the insert member having a downwardly facing opening for snapping over the head when the tongue is inserted in the channel.

17. A method of mounting a denture assembly in an oral cavity, comprising the steps of:

forming a vertically extending cut-out in the side face of an existing cuspid or molar tooth adjacent the site at which the denture assembly is to be mounted, the cut-out corresponding in shape substantially with the shape of a retainer member for mounting in the cut-out and being substantially parallel with the intended path of insertion of the denture assembly;

securing a vertically extending insert member to one end of the denture assembly by means of a tail portion projecting from the insert member;

sliding a tongue on one of the members into a channel on the other member until a head at one end of one of the members snap fits into a corresponding socket at the end of the other member;

placing bonding material on at least part of the exposed faces of the cut-out and corresponding faces of the retainer member; and sliding the retainer member carrying the denture assembly via the connected insert member vertically into the cut-out so that the denture assembly is properly aligned in the oral cavity and the retainer member is secured in the cut-out by the bonding material.

18. The method as claimed in claim 17, including the further steps of:

securing a further insert member to another end tooth of the denture assembly via a tail portion projecting from the insert member, connecting the further insert member to a further retainer member by sliding the tongue on one of the members into a corresponding channel on the other member until a head at the end of one of the members snap-fits into a corresponding socket at the lower end of the other member;

preparing a cut-out in the side wall of a second existing tooth to which the further insert and retainer members are to be secured, the second cut-out being substantially parallel with the first;

placing bonding material against at least part of the corresponding surfaces of the second retainer member and tooth cut-out;

mounting the denture assembly in the oral cavity by inserting the second retainer member in the second tooth cut-out in parallel with the path of insertion of the first retainer member and securing the second retainer member in the second tooth cut-out.

19. The method as claimed in claim 17, wherein the step of sliding the retainer member vertically into the cut-out comprises first securing an alignment fork in opposed grooves provided on the insert member, holding the handle of the fork to slide the retainer member into the cut-out, and removing the fork from the insert member grooves when the insertion is completed.

* * * * *